(12) United States Patent
Comee et al.

(10) Patent No.: US 11,877,739 B2
(45) Date of Patent: Jan. 23, 2024

(54) PNEUMATIC OR HYDRAULIC POWERED TISSUE CLOSURE DEVICES

(71) Applicant: Boston Scientific Scimed, Inc., Maple Grove, MN (US)

(72) Inventors: Shaun D. Comee, Fiskdale, MA (US); Kathryn Venuto, Waltham, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 335 days.

(21) Appl. No.: 16/952,765

(22) Filed: Nov. 19, 2020

(65) Prior Publication Data
US 2021/0145434 A1 May 20, 2021

Related U.S. Application Data

(60) Provisional application No. 62/937,980, filed on Nov. 20, 2019.

(51) Int. Cl.
*A61B 17/068* (2006.01)
*A61B 17/04* (2006.01)
(Continued)

(52) U.S. Cl.
CPC .... *A61B 17/0469* (2013.01); *A61B 17/00234* (2013.01); *A61B 17/068* (2013.01);
(Continued)

(58) Field of Classification Search
CPC ............. A61B 17/068; A61B 17/072; A61B 17/07207; A61B 17/0469; A61B 17/115;
(Continued)

(56) References Cited

U.S. PATENT DOCUMENTS 4,621,639 A 11/1986 Transue et al.
5,657,921 A 8/1997 Young et al.
(Continued)

FOREIGN PATENT DOCUMENTS

| EP | 1884201 A1 | 2/2008 |
|---|---|---|
| EP | 2689731 A2 | 1/2014 |
| EP | 3342355 A1 | 7/2018 |

OTHER PUBLICATIONS

International Search Report and Written Opinion for the International Patent Application No. PCT/US2020/061264, dated May 26, 2021, 28 pages.

(Continued)

*Primary Examiner* — Scott A Smith
(74) *Attorney, Agent, or Firm* — Seager, Tufte & Wickhem, LLP

(57) ABSTRACT

The present disclosure relates generally to systems, medical devices, and methods for closing an opening in a target tissue using hydraulics and/or pneumatics. In some embodiments, a medical device may include an endoscopic device operable to close an opening in a target tissue, and an actuator operable with the endoscopic device, wherein the actuator includes a piston within a chamber. The piston may include a piston head engaged with an interior surface of the chamber, and a piston rod coupled to a tissue engagement component of the endoscopic device, wherein pressure from a fluid within the chamber actuates the tissue engagement component.

12 Claims, 6 Drawing Sheets

(51) Int. Cl.
*A61B 17/00* (2006.01)
*A61B 17/072* (2006.01)

(52) U.S. Cl.
CPC ........ *A61B 17/0686* (2013.01); *A61B 17/072* (2013.01); *A61B 17/07207* (2013.01); *A61B 2017/00323* (2013.01); *A61B 2017/00539* (2013.01); *A61B 2017/00544* (2013.01); *A61B 2017/07214* (2013.01); *A61B 2017/07228* (2013.01)

(58) Field of Classification Search
CPC ........... A61B 2017/07214; A61B 2017/00539; A61B 2017/00544; A61B 2017/07228
USPC ..... 227/19, 176.1, 175.1, 180.1; 606/1, 139, 606/219
See application file for complete search history.

(56) References Cited

U.S. PATENT DOCUMENTS

| | | | |
|---|---|---|---|
| 6,074,404 | A | 6/2000 | Stalker et al. |
| 9,433,417 | B2 | 9/2016 | Kneifel et al. |
| 9,913,648 | B2 | 3/2018 | Shelton, IV et al. |
| 2008/0029572 | A1* | 2/2008 | Shelton ................ A61B 17/072 227/175.1 |
| 2012/0101483 | A1 | 4/2012 | Klaffenboeck et al. |
| 2012/0181322 | A1 | 7/2012 | Whitman et al. |
| 2014/0027492 | A1* | 1/2014 | Williams ......... A61B 17/07207 227/176.1 |
| 2015/0136835 | A1 | 5/2015 | Shelton et al. |
| 2018/0235604 | A1 | 8/2018 | Comee et al. |
| 2019/0029668 | A1 | 1/2019 | Meade et al. |
| 2019/0083086 | A1 | 3/2019 | Klaffenbock et al. |

OTHER PUBLICATIONS

Anonymous: "Mechanical Systems Class Notes 2.0—An understanding of mechanical advantage and work helps in determining the efficiency of machines 2.1—Machines Make Work Easier" Jul. 10, 2019—Retrieved from Internet: URL: https://web.archive.org/web/20190710232814if_/http:www.edquest.ca:80/pdf/sia84-2notes.pdf.

* cited by examiner

PNEUMATIC OR HYDRAULIC POWERED TISSUE CLOSURE DEVICES

CROSS-REFERENCE TO RELATED APPLICATIONS

The present application claims the benefit of priority under 35 U.S.C. § 119 to U.S. Provisional Patent Application No. 62/937,980, filed Nov. 20, 2019, which application is incorporated herein by reference in its entirety for all purposes.

FIELD

The present disclosure relates to the treatment of tissue defects, and, more particularly, to systems, devices, and methods for assisted tissue closure.

BACKGROUND

In some medical procedures, it is beneficial to fixedly connect a portion of tissue to another portion of tissue, such as to hold together a wound or damaged tissue. For example, one or more sutures or staples may be used to connect tissue portions. Often, an assembly, including staples, or a needle, and a suture coupled to the needle, is used to secure tissue together.

Furthermore, both suturing and stapling closure methods are desirable for tissue resection or various bariatric procedures. One drawback with suturing and stapling systems is the challenge of deliverable force to the distal end of the system. It is with these considerations in mind that a variety of advantageous medical outcomes may be realized by the devices, systems, and methods of the present disclosure.

SUMMARY

In one or more embodiments, a medical device may include an endoscopic device operable to close an opening in a target tissue and an actuator operable with the endoscopic device, the actuator including a piston within a chamber. The piston may include a piston head engaged with an interior surface of the chamber, and a piston rod coupled to a tissue engagement component of the endoscopic device, wherein pressure from a fluid within the chamber actuates the tissue engagement component. In some embodiments, the fluid is a gas or a liquid. In some embodiments, the actuator further comprises a valve operable to permit the fluid to enter the chamber, wherein the valve controls a flow of the fluid through an inlet conduit and an outlet conduit, and wherein the inlet conduit and the outlet conduit are fluidly connected with the chamber. In some embodiments, the tissue engagement component is a needle passer or an endoscopic stapler head. In some embodiments, the endoscopic device is a suturing device, the suturing device including an elongate member, and a suture arm at one end of the elongate member, wherein the needle passer is operable to deliver a needle between the elongate member and a distal end of the suture arm for suturing the target tissue. In some embodiments, the piston rod is disposed within an interior of the elongate member, and wherein the piston rod is coupled to the needle passer. In some embodiments, the fluid within the chamber impacts the piston head to actuate the piston rod and the needle passer in an axial direction. In some embodiments, the endoscopic stapler head may include a first jaw opposite a second jaw, wherein the piston rod is coupled to the first jaw, and a staple cartridge along the second jaw, wherein movement of the piston rod causes the first jaw to make or break contact with the staple cartridge. In some embodiments, the actuator may further include a second piston within a second chamber, wherein the second chamber is fluidly connected with the first chamber, and wherein a first diameter of the first chamber is larger than a second diameter of the second chamber. In some embodiments, the second piston may include a second piston head engaged with an interior surface of the second chamber, and a second piston rod extending from the second piston head, wherein the second piston head faces the piston head.

In one or more embodiments, a system may include an endoscope and a device including an actuator operable to close an opening in a target tissue. The actuator may include a piston within a chamber, the piston including a piston head engaged with an interior surface of the chamber, and a piston rod coupled to a tissue engagement component of the endoscopic device, wherein pressure from a fluid within the chamber actuates the piston rod and the tissue engagement component. In some embodiments, the actuator may further include a valve operable to permit the fluid to enter the chamber, wherein the valve controls a flow of the fluid through an inlet conduit and an outlet conduit fluidly connected with the chamber. In some embodiments, the device may further include a suturing needle passer or an endoscopic stapler head. In some embodiments, the device may be a suturing device, wherein the suturing device includes an elongate member and a suture arm at one end of the elongate member, wherein the tissue engagement component is a needle passer operable to deliver a needle between the elongate member and a distal end of the suture arm for suturing the target tissue. In some embodiments, the device may be a stapler head, the stapler head including a first jaw opposite a second jaw, wherein the piston rod is coupled to the first jaw, and a staple cartridge along the second jaw, wherein movement of the piston rod causes the first jaw to make or break contact with the staple cartridge. In some embodiments, the actuator may further include a second piston within a second chamber, wherein the second chamber is fluidly connected with the first chamber, and wherein a first diameter of the piston head is larger than a second diameter of a second piston head of the second piston.

In one or more embodiments, a method may include inserting an endoscopic medical device within a patient, the endoscopic medical device including an endoscopic device operable to engage a target tissue, and an actuator coupled to the endoscopic device, the actuator including a piston within a chamber. The piston may include a piston head engaged with an interior surface of the chamber, and a piston rod coupled to a tissue engagement component of the endoscopic device. The method may further include controlling an amount of a fluid within the chamber to actuate the piston rod and the tissue engagement component relative to the target tissue, and engaging the target tissue with the tissue engagement component to close an opening of the target tissue. The method may further include engaging the target tissue using a suturing device, the suturing device including an elongate member and a suture arm at one end of the elongate member, wherein the tissue engagement component is a needle passer containing a needle. The method may further include delivering the needle between the elongate member and a distal end of the suture arm to close the opening of the target tissue. The method may further include engaging the target tissue using a stapler head, the stapler head including a first jaw opposite a second jaw, wherein the piston rod is coupled to the first jaw, and actuating the piston rod to close the first and second jaws about the target tissue to close the opening of the target tissue. The method may further include providing a second piston within a second chamber, wherein the second chamber is fluidly connected with the first chamber, and wherein a first diameter of the piston head is larger than a second diameter of a second piston head of the second piston, and actuating the second piston to increase a pressure of the fluid in the second chamber and the chamber.

Various one or more of the features summarized above, may be interchanged, exchanged, combined, or substituted with, or for, other features summarized above, for use in connection with the medical systems and methods summarized above, and with respect to the embodiments described in greater detail below and embodiments otherwise within the scope of the present disclosure.

BRIEF DESCRIPTION OF THE DRAWINGS

Non-limiting embodiments of the present disclosure are described by way of example with reference to the accompanying figures, which are not intended to be drawn to scale. In the figures, each identical or nearly identical component illustrated is typically represented by a single numeral. For purposes of clarity, not every component is labeled in every figure, nor is every component of each embodiment shown where illustration is not necessary to allow those of ordinary skill in the art to understand the disclosure. Furthermore, some of the figures include cross-sectional views in the form of "slices", or "near-sighted" cross-sectional views, omitting certain background lines or features otherwise visible in a "true" cross-sectional view, for illustrative clarity. In the figures.

DETAILED DESCRIPTION

Figure 1:
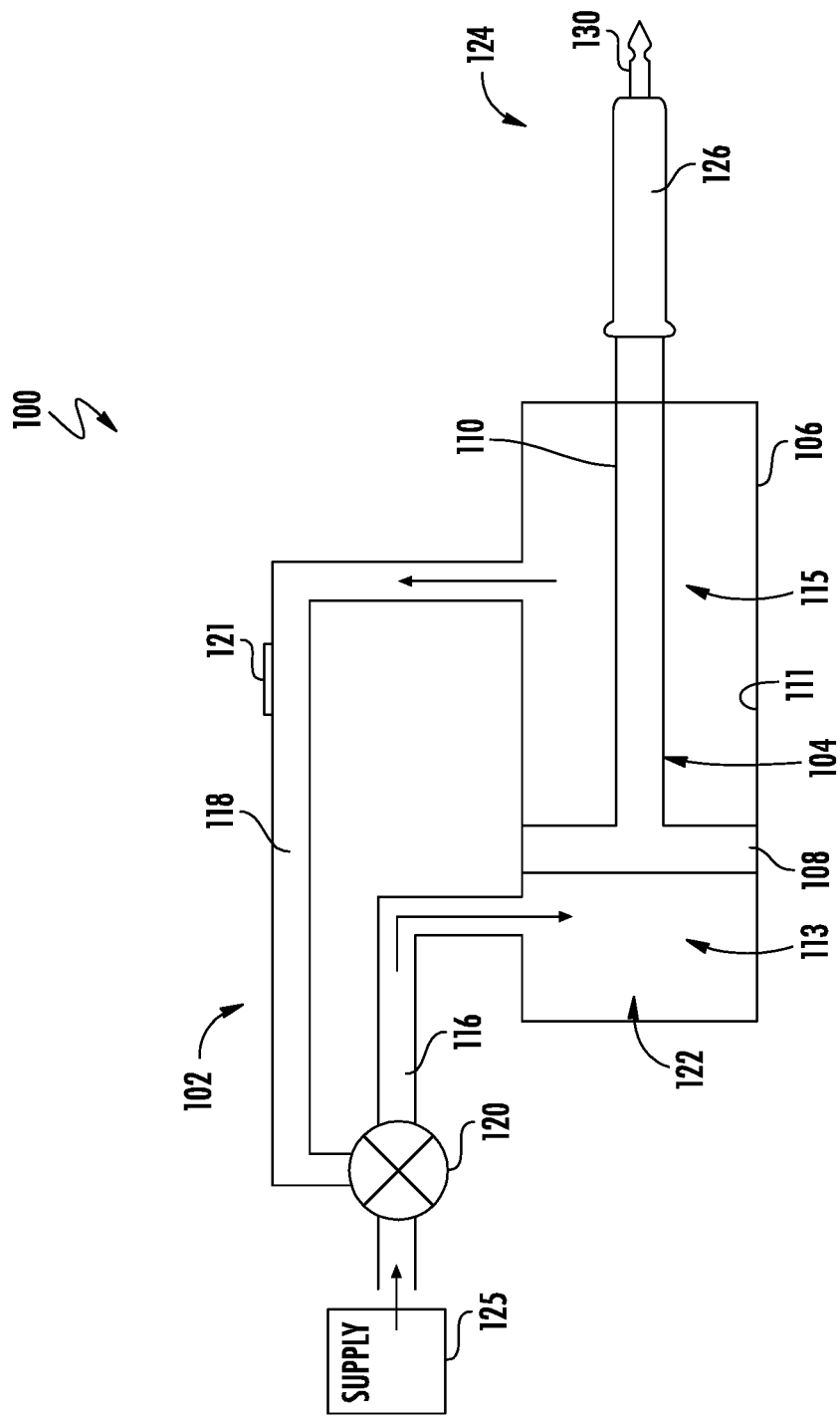
FIG. 1 is a side cross-sectional view of an actuator of a medical device according to embodiments of the present disclosure.

The present disclosure is not limited to the particular embodiments described herein. The terminology used herein is for the purpose of describing particular embodiments only, and is not intended to be limiting beyond the scope of the appended claims. Unless otherwise defined, all technical terms used herein have the same meaning as commonly understood by one of ordinary skill in the art to which the disclosure belongs.

One trend in medicine includes moving from laparoscopic and open surgical procedures to miniaturized, endoscopic procedures. Endoscopists can perform ever more complex procedures noninvasively and under direct visualization. As a result, there exists a need for endoscopic medical devices possessing specific built-in treatment capabilities. Such medical devices would facilitate both a broad range of procedural interventions more prevalent in hospitals, and further lead to the development of significantly more complex and capable scope designs.

Embodiments herein address at least the above deficiencies by integrating complex functions into either a single-use scope or reusable endoscope. For example, the functions available according to the systems, medical devices, and methods of the present disclosure may include one or more of the following: suturing, stapling, cutting, cauterizing, clip deployment, injection, tissue manipulation, and more. Furthermore, by using the suture devices disclosed herein only a single time, the infection risk can be greatly minimized.

The disclosure pertains to medical devices, e.g., endoscopes, gastroscopes, bronchoscopes, colonoscopes, ureteroscopes, endoscopic stapler heads, and the like, having integrated features for acquiring, manipulating, and closing openings in target tissue. Although single-use endoscope medical devices are described herein, it is understood that embodiments of the present disclosure may be included in reusable medical devices such as endoscopes as well. Embodiments herein address at least the above deficiencies by integrating complex functions into a single medical device.

Furthermore, embodiments herein address at least the above deficiencies of the prior art, such as the elevated level of force required to actuate a stapler head or push a needle through tissue. Prior art systems use either pull wires or the force that an operator can apply by pushing and/or pulling on a catheter or similar. These prior art actuation methods can be unreliable in tortuous anatomy, translate too small a force to the distal end of the device, and/or be fatiguing to the operator. Embodiments of the present disclosure enable higher forces, which may be required at a distal end of the medical device, by introducing pneumatics and/or hydraulics into suturing or stapling devices. Pneumatics and hydraulics can increase the force applied at a proximal end user interface, thus allowing distal end mechanisms to more easily puncture tissue or similar. Embodiments included herein describe various configurations that support either suturing or stapling-based devices. However, it is recognized that the end use is not so limited, and the general ideas and designs may be applied to many similar devices and end effectors requiring similar force and motions.

With reference to FIG. 1, an actuator 102 of a system or endoscopic medical device (hereinafter "device") 100 according to embodiments of the disclosure will be described. As shown, the actuator 102 may include a piston 104 within a chamber 106, the piston 104 having a piston head 108 connected with a piston rod 110. The piston head 108 may engage an interior surface 111 of the chamber 106, generally dividing the chamber 106 into a first portion 113, and a second portion 115. As shown, the first portion 113 of the chamber 106 may be fluidly connected with an inlet conduit 116, while the second portion 115 of the chamber 106 may be fluidly connected with an outlet conduit 118. In some embodiments, a pressure difference between the first portion 113 and the second portion 115 of the chamber 106 will cause the piston 104 to move axially (e.g., left or right in the figure) within the chamber 106.

The actuator 102 may further include a valve 120 operable to permit a fluid 122 from a fluid supply 125 to enter and exit the chamber 106. More specifically, the valve 120 may control the flow of the fluid 122 through both the inlet conduit 116 and the outlet conduit 118. Although not shown, the valve 120 may be controlled at a handle or user interface of the device 100. In some embodiments, the outlet conduit 118 may include one or more relief valves 121, while the inlet conduit 116 may be connected to the fluid supply 125 for delivering the fluid 122 to the chamber 106. Although non-limiting, the fluid 122 may be pressured air or $CO_2$.

Figure 2A:
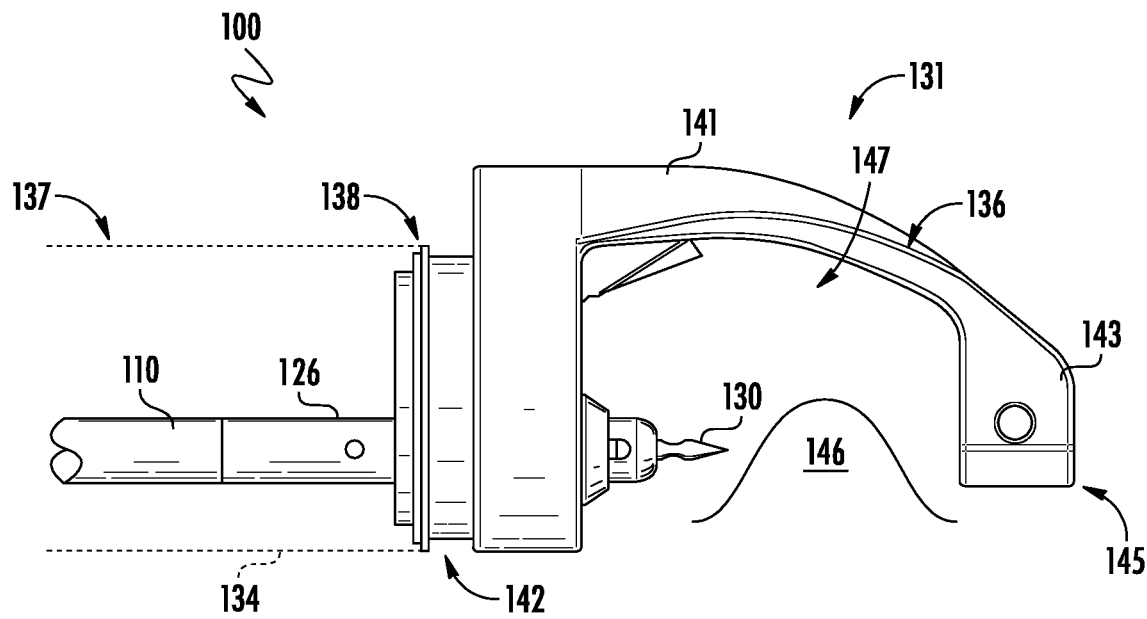
FIG. 2A is a side view of an endoscopic device in a first state according to embodiments of the present disclosure.
Figure 2B:
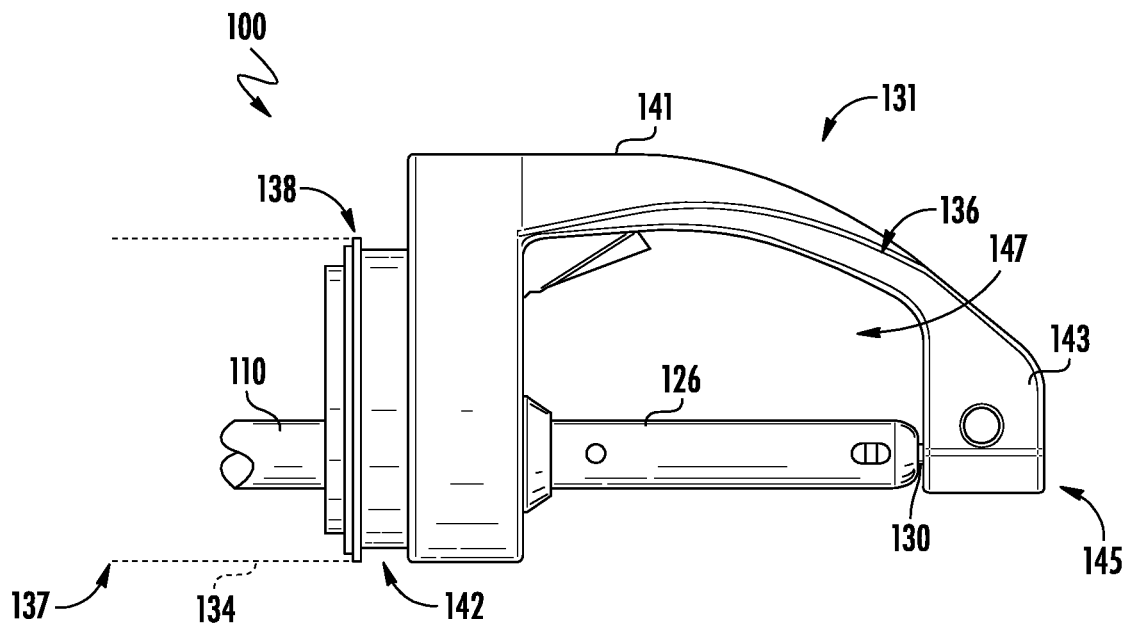
FIG. 2B is a side view of the endoscopic device of FIG. 2A in a second state according to embodiments of the present disclosure.

As shown, the piston rod 110 may be coupled to a tissue engagement component 124. In non-limiting embodiments, as shown in FIGS. 2A and 2B, the tissue engagement component 124 may be a needle passer 126 of an endoscopic device, such as a suturing device 131. In some embodiments, the needle passer 126 may contain, or be coupled with, a needle 130 operable to engage a target tissue. The device 100 may further include the suturing device 131 coupled to the piston rod 110 of the actuator 102. In some embodiments, the suturing device 131 may include an elongate member 134 coupled to, or integrally formed with, a suture arm 136. The elongate member 134 may be a flexible hollow tube, endoscope, catheter, etc., and may include a proximal end 137 opposite a distal end 138. In some embodiments, the elongate member 134 may be a flexible material, such as silicone, a thermoplastic elastomer including polyamide and polyether backbone blocks, polyurethane, etc., to allow for scope flexing. In other embodiments, the elongate member 134 may be a rigid material, such as polycarbonate, acrylonitrile butadiene styrene (ABS), etc., to provide a more direct positioning response.

In some embodiments, the suture arm 136 may be part of a distal assembly, including a body 141 having a proximal section 142 extending from the distal end 138 of the elongate member 134. The proximal section 142 and the elongate member 134 may be integrally connected such that the body 141 and the elongate member 134 form an integrated, single use device. In other embodiments, the distal assembly may be removably coupleable to the elongate member 134 of a single use or a reusable device.

As further shown, the suture arm 136 may extend to an endcap 143, which is configured to releasably engage and disengage the needle 130. In some embodiments, the needle 130 may be delivered by the needle passer 126 between the distal end 138 of the elongate member 134 and the endcap 143, which is located at a distal end 145 of the suture arm 136. The needle 130 may be connected to a suture (not shown) used for tensioning and closing an opening in a target tissue 146 (FIG. 2A) retained within a suture cavity 147 defined by the suture arm 136.

With reference to FIGS. 1, 2A, and 2B, operation of the device 100 will be described in greater detail. In some embodiments, the device 100 may be a pneumatic device employing a compressible fluid, such as air, to drive operation of the piston 104. Initially, the needle passer 126 and the needle 130 may be recessed in a position adjacent the proximal section 142 of the body 141, as demonstrated in FIG. 2A. Once the target tissue 146 is retained within the suture cavity 147, e.g., by a tissue grasper (not shown) delivered through a channel of the body 141, the valve 120 may be opened to cause an increase in the volume of the fluid 122 within the first portion 113 of the chamber 106. As the volume of the fluid 122 increases, increased pressure upon the piston head 108 causes the piston 104, the needle passer 126, and the needle 130 to be biased towards the target tissue 146. The needle 130 may then puncture the target tissue 146 before being retained within the endcap 143, as shown in FIG. 2B. Depending on the size and type of tissue opening, the needle 130 may be passed back and forth between the proximal section 142 and distal end 145 of the suture arm 136, the needle 130 including one or more pointed tips for puncturing the target tissue 146 with each pass.

Figure 3:
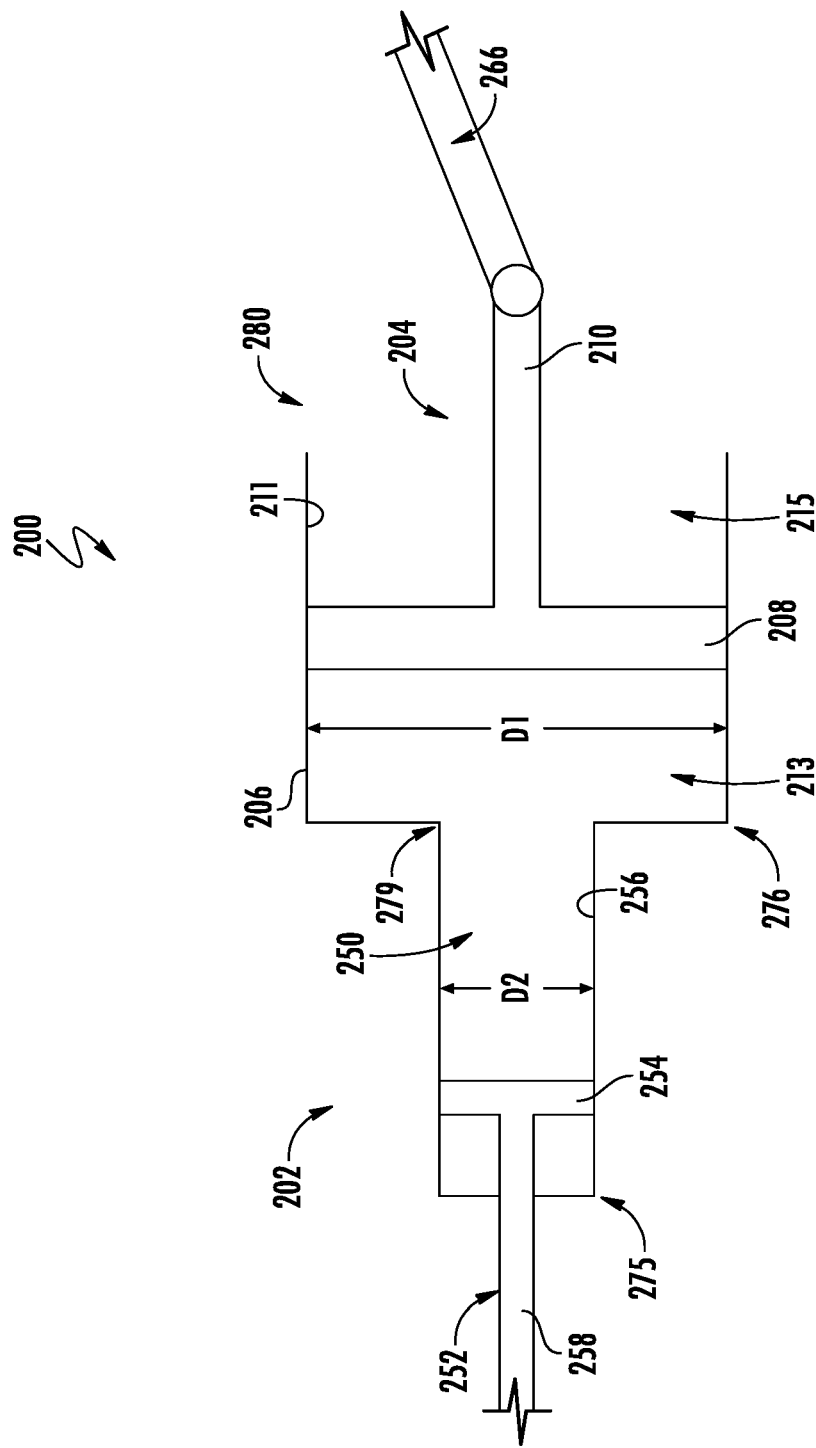
FIG. 3 is a side cross-sectional view of another actuator for use with a medical device according to embodiments of the present disclosure.

Turning now to FIG. 3, an actuator 202 of an endoscopic medical device (hereinafter "device") 200 according to embodiments of the disclosure will be described in greater detail. As shown, the actuator 202 may include a first piston 204 within a first chamber 206, the first piston 204 having a first piston head 208 connected with a first piston rod 210. The first piston head 208 may extend across an entire interior area of the first chamber 206, engaging an interior surface 211 thereof. As shown, the first piston head 208 may generally divide the first chamber 206 into a first portion 213 and a second portion 215.

As shown, the first portion 213 of the first chamber 206 may be fluidly connected with a second chamber 250 containing a second piston 252. The second piston 252 may include a second piston head 254 engaged with an interior surface 256 of the second chamber 250, and a second piston rod 258 extending from the second piston head 254. In some embodiments, the second piston rod 258 may extend outside the second chamber 250. As shown, the second piston head 254 faces the first piston head 208.

In some embodiments, a first diameter 'D1' of the first chamber 206 is larger than a second diameter 'D2' of the second chamber 250, thereby providing a mechanical advantage, or force multiplication, during uses of the first and second pistons 204, 252. It will be appreciated that the device 200 may be a hydraulic device employing an incompressible hydraulic liquid such as oil or water to drive operation of the first and second pistons 204, 252. During use, a smaller input force on the second piston 252 results in a greater output force on the first piston 204, thereby reducing an initial force required by a user. In some embodiments, the second piston 252 may be controlled by any variety of actuators (e.g., a lever) located at a user interface (not shown). Furthermore, in other embodiments, one or more additional pistons may be employed to provide more force multiplication.

Figure 4A:
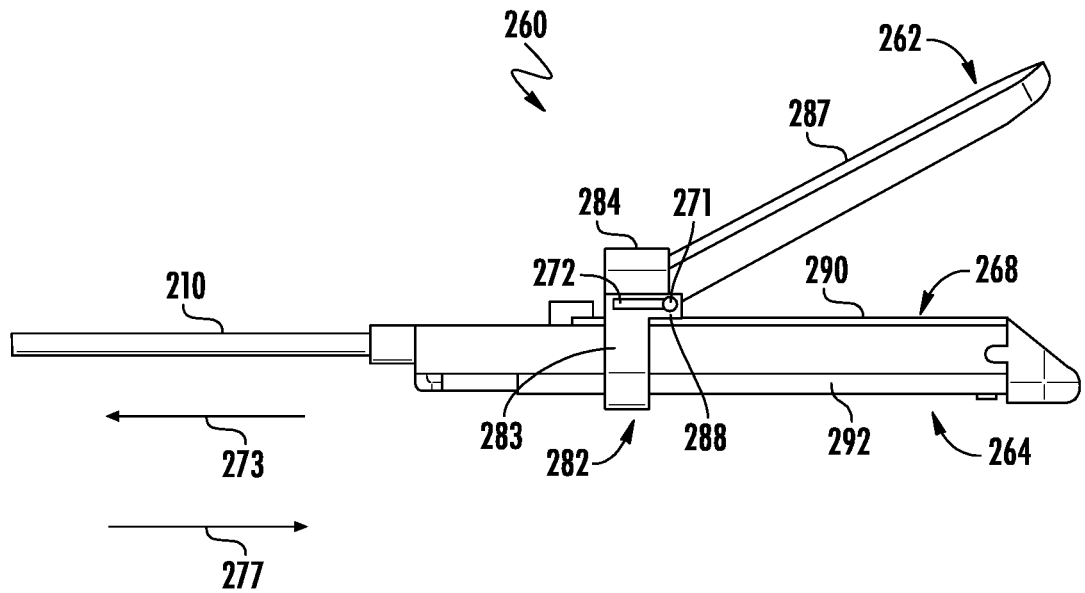
FIG. 4A is a side view of an endoscopic device in a first state according to embodiments of the present disclosure.
Figure 4B:
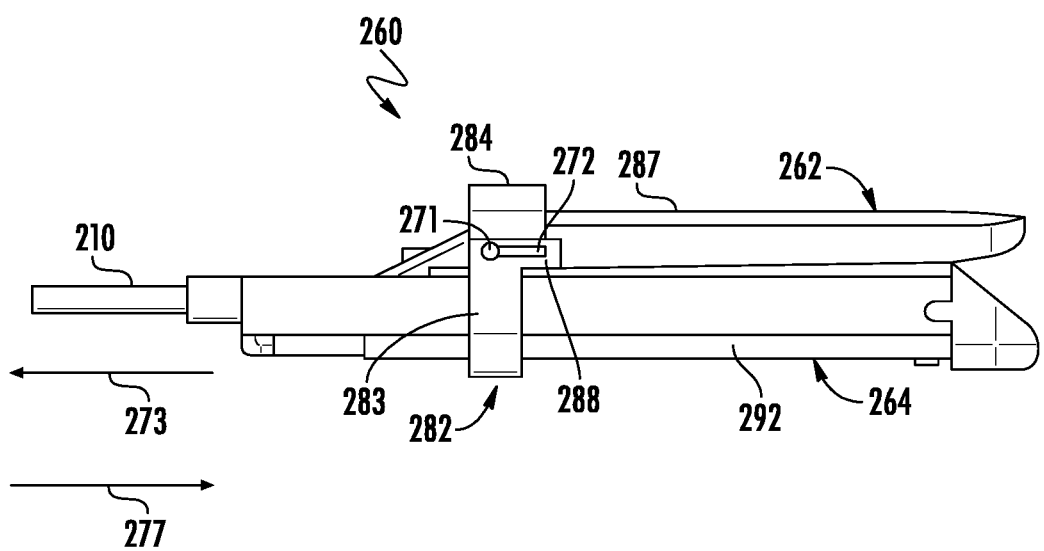
FIG. 4B is a side view of the endoscopic device of FIG. 4A in a second state according to embodiments of the present disclosure.

With reference now to FIGS. 3, 4A, and 4B, an endoscopic stapler head 260 according to embodiments of the present disclosure will be described. As shown, the first piston rod 210 may be coupled to the endoscopic stapler head 260. In non-limiting embodiments, the endoscopic stapler head 260 includes a first jaw 262 opposite a second jaw 264. The first jaw 262 and/or the second jaw 264 may be coupled to the first piston rod 210, for example, via one or more mechanical linkages 266 (FIG. 3) for connecting the stapler head 260 to the actuator 202.

In some embodiments, the endoscopic stapler head 260 may include a staple cartridge 268 along an interior of the second jaw 264, wherein movement of the first piston rod 210 causes the first jaw 262, sometimes referred to as an anvil, to engage or disengage with the staple cartridge 268. The first and second jaws 262, 264 are pivotally attached to one another to clamp a target tissue (not shown) to the staple cartridge 268. More specifically, the endoscopic stapler head 260 may be provided in an initial position, as shown in FIG. 4A, in which the first piston rod 210 and the mechanical linkage 266 may be drawn back along a first direction 273 (e.g., towards a handle or user interface). The mechanical linkage 266 may be connected to a biasing device (e.g., a slider) 282 having a first section 283 coupled to the second jaw 264 and a second section 284 coupled to or extending around the first jaw 262. In some embodiments, the second section 284 may include a shroud having an opening for the first jaw 262. As the biasing device 282 moves relative to the first jaw 262, an inner surface of the second section 284 may engage an outer surface 287 of the first jaw 262, thereby forcing the first jaw 262 to close. In some embodiments, the first jaw 262 also moves or pivots within the second section 284 of the biasing device 282 via a pin 271 of the first jaw 262 that slides within a pin slot 272 of the biasing device 282.

As further shown, the first section 283 of the biasing device 282 may include a flange 288 engaged with a ledge 290 of the second jaw 264. The biasing device 282 may be further engaged with the second jaw 264 along a second flange 292. Embodiments herein are not limited in this context, however.

In some embodiments, to open the endoscopic stapler head 260, the second piston 252 may be biased towards a proximal end 275 of the second chamber 250, causing a decreased pressure within the second chamber 250 and the first portion 213 of the first chamber 206. The decreased pressure in turn may cause the first piston head 208 to move axially towards a proximal end 276 of the first chamber 206. As the first piston head 208 moves towards the proximal end 276 of the first chamber 206, so does the first piston rod 210 and the mechanical linkage 266, causing the biasing device 282 to move along the first direction 273. Without the second section 284 of the biasing device 282 engaged with the outer surface 287 of the first jaw 262, the first jaw 262 may be free to pivot away from the second jaw 264, for example, in response to a spring force or lever mechanism.

In other embodiments, the first piston rod 210 and the mechanical linkage 266 may be coupled to the first jaw 262. During use, pulling the first piston rod 210 along the first direction 273 may pull the first jaw 262 within the first section 283 of the biasing device 282 to lock the first jaw 262 in a closed position. In some embodiments, a separate piston rod (not shown), may be coupled to the biasing device 282 to staple and cut tissue by the first and second jaws 262, 264 as the biasing device 282 moves in a second direction 277 (e.g., away from a handle or user interface).

To close the endoscopic stapler head 260, as depicted in FIG. 4B, the first piston rod 210, the mechanical linkage 266, and the biasing device 282 may be biased in the second direction 277. To accomplish this, the second piston 252 may be biased towards a distal end 279 of the second chamber 250, causing an increased pressure within the second chamber 250 and the first portion 213 of the first chamber 206. The increased pressure in turn may cause the first piston head 208 to move axially towards a distal end 280 of the first chamber 206. As the first piston head 208 moves towards the distal end 280 of the first chamber 206, so does the first piston rod 210 and the mechanical linkage 266, causing the biasing device 282 to move in the second direction 277, thus causing the first jaw 262 to pivot or rotate towards the second jaw 264.

As the endoscopic stapler head 260 closes, the first jaw 262 may deform staples (not shown) driven up from staple holes in the staple cartridge 268 into a closed shape. When the endoscopic stapler head 260 is in a closed position, its cross-sectional area, as well as the first piston rod 210, may be suitable for insertion through a small surgical opening, such as through a cannula of a trocar. Alternatively, the stapler head 260 may be inserted into a body opening via attachment to the end of a scope, or inserted through a working channel of the scope. In some embodiments, correct placement and orientation of the endoscopic stapler head 260 is facilitated by controls on the handle/user interface.

Although the endoscopic stapler head 260 is shown as being biased by the actuator 202, it will be appreciated that the endoscopic stapler head 260 could be coupled to the actuator 102 shown in FIG. 2 and described herein. For example, the piston rod 110 of the actuator 102 could be coupled to the mechanical linkage 266, which is used to control the first jaw 262. Alternatively, the suturing device 131 shown in FIGS. 2A- and 2B and described herein, could be biased by the actuator 202. For example, the first piston rod 210 may be coupled to the needle passer 126. Embodiments herein are not limited in this context.

Figure 5:
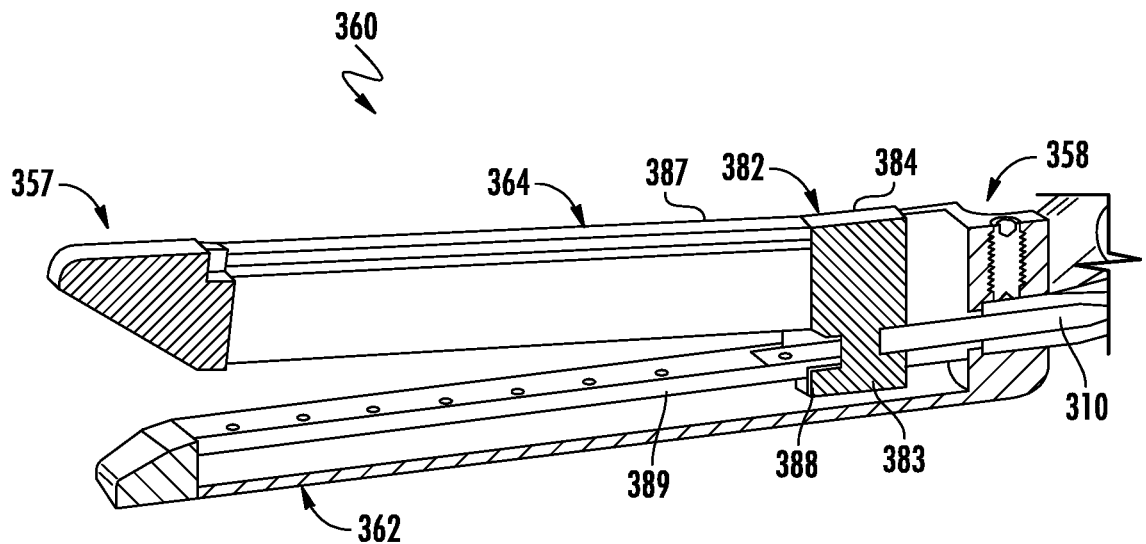
FIG. 5 is a perspective view of an endoscopic stapler head according to embodiments of the present disclosure.

Turning to FIG. 5, an alternative endoscopic stapler head 360 according to embodiments of the present disclosure, will be described. As shown, the endoscopic stapler head 360 may include a first jaw 362 opposite a second jaw 364, and a biasing device 382 coupled to a piston rod 310, which may be the same or similar to the first piston rod 210 and/or mechanical linkage 266 of FIGS. 4A and 4B for connecting the stapler head 360 to the actuator 202.

The biasing device (e.g., a slider) 382 may have a first section 383 coupled to the first jaw 362 and a second section 384 coupled to the second jaw 364. In some embodiments, the first section 383 may include a flange 388 engaged with a protrusion or ledge 389 of the first jaw 362. During use, the piston rod 310 causes the biasing device 382 to move between a distal end 357 and a proximal end 358 of the endoscopic stapler head 360. As the biasing device 382 traverses along the first jaw 362 and the second jaw 364, an inner surface of the second section 384 may engage an outer surface 387 of the second jaw 364 to bring the first jaw 362 and the second jaw 364 together.

Figure 6:
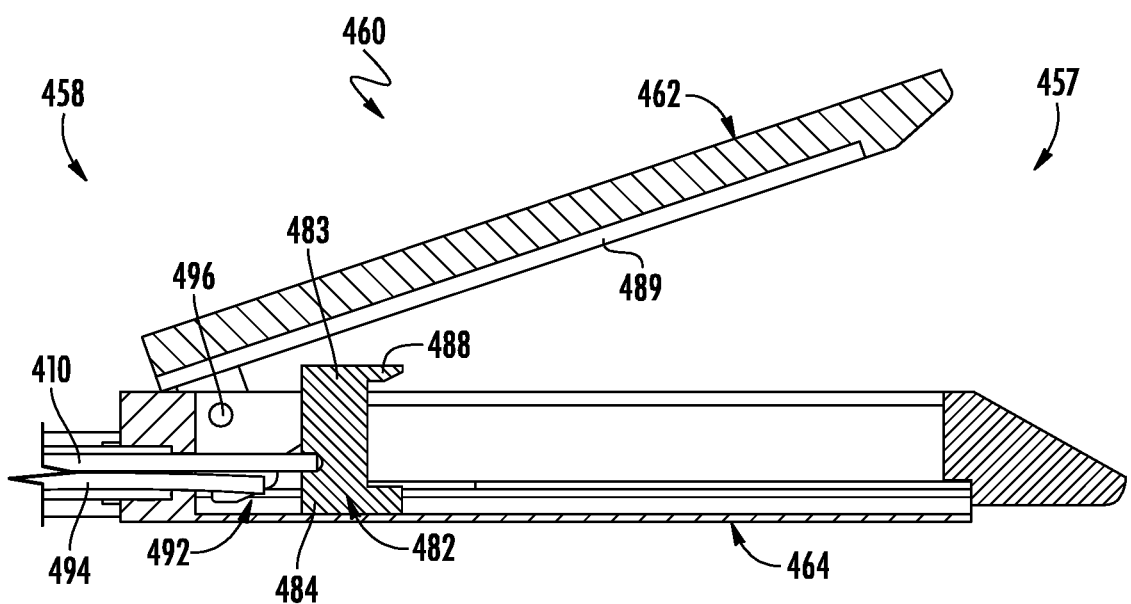
FIG. 6 is a perspective view of an endoscopic stapler head according to embodiments of the present disclosure.

Turning to FIG. 6, another alternative endoscopic stapler head 460 according to embodiments of the present disclosure will be described. As shown, the endoscopic stapler head 460 may include a first jaw 462 opposite a second jaw 464, and a biasing device 482 coupled to a piston rod 410, which may be the same or similar to the first piston rod 210 and/or mechanical linkage 266 of FIGS. 4A- and 4B for connecting the stapler head 460 to the actuator 202.

Although shown disengaged with the first jaw 462 in FIG. 6, the biasing device (e.g., a slider) 482 may have a first section 483 coupleable with the first jaw 462 and a second section 484 coupled to the second jaw 464. In some embodiments, the first section 483 may include a flange 488 operable to slide along a protrusion or ledge 489 of the first jaw 462. During use, the piston rod 410 causes the biasing device 482 to move between a distal end 457 and a proximal end 458 of the endoscopic stapler head 460. As the biasing device 482 traverses along the first jaw 462 and the second jaw 464, the first jaw 462 and the second jaw 464 are brought together to staple and cut tissue.

In the non-limiting embodiment shown, the stapler head 460 may further include a pivot arm 492 coupled between the first jaw 462 and a second piston rod 494. The second piston rod 494 may be biased by an actuator, such as the actuator 102 or the actuator 202 described herein. The pivot arm 492 may be fixed to rotate about a pivot point 496, wherein movement of the second piston rod 494 towards the distal end 457 of the stapler head 460 causes the first jaw 462 to open, and movement of the second piston rod 494 towards the proximal end 458 causes the first jaw 462 to close.

Figure 7:
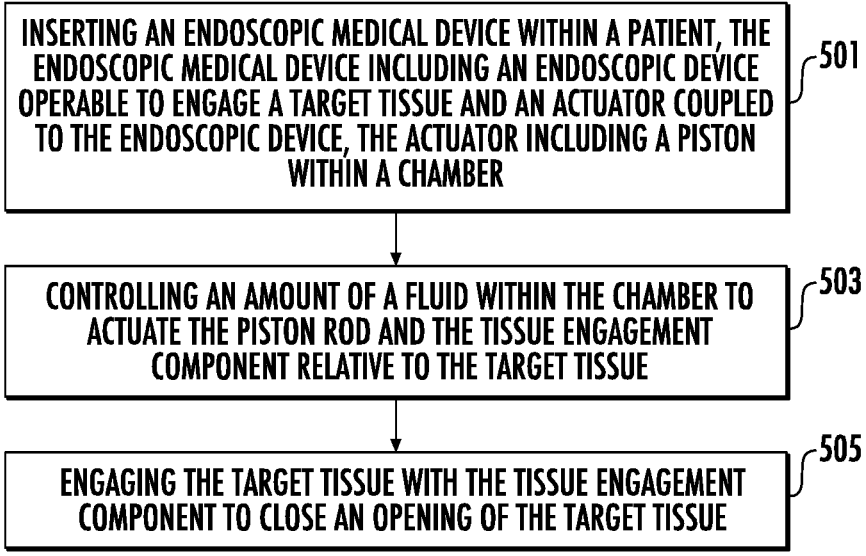
FIG. 7 is a flow diagram of a method according to embodiments of the present disclosure.

FIG. 7 is a flow diagram of a method 500 according to embodiments of the present disclosure. At block 501, the method 500 may include inserting an endoscopic medical device within a patient, the endoscopic medical device including an endoscopic device operable to engage a target tissue and an actuator coupled to the endoscopic device, the actuator including a piston within a chamber. In some embodiments, the piston may include a piston head engaged with an interior surface of the chamber, and a piston rod coupled to a tissue engagement component of the endoscopic device. In some embodiments, the method may include providing a second piston within a second chamber, wherein the second chamber is fluidly connected with the first chamber, and wherein a first diameter of the piston head is larger than a second diameter of a second piston head of the second piston. The method may further include actuating the second piston to increase a pressure of the fluid in the second chamber and the first chamber.

At block 503, the method may include controlling an amount of a fluid within the chamber to actuate the piston rod and the tissue engagement component relative to the target tissue. In some embodiments, a valve may be opened/closed to control the fluid entering the chamber. In some embodiments, the actuator may include an inlet conduit and an outlet conduit fluidly connected with the chamber, wherein the inlet conduit is positioned along a first side of the piston head, and wherein the outlet conduit is positioned along a second side of the piston head.

At block 505, the method 500 may include engaging the target tissue with the tissue engagement component to close an opening of the target tissue. In some embodiments, the method may include engaging the target tissue using a suturing device, the suturing device including an elongate member, and a suture arm at one end of the elongate member, wherein the tissue engagement component is a needle passer containing a needle. The method may further include delivering the needle between the elongate member and a distal end of the suture arm to close the opening of the target tissue. In some embodiments, the method may include engaging the target tissue using a stapler head, the stapler head including a first jaw opposite a second jaw, wherein the piston rod is coupled to the first jaw. The method may further include actuating the piston rod to close the first and second jaws about the target tissue to close the opening of the target tissue.

It will be appreciated that a variety of different materials may be used in forming the devices described herein. In some cases, a variety of different metals may be used. Illustrative but non-limiting examples of suitable metals include titanium, stainless steel, magnesium, cobalt chromium and others. In some embodiments, for example, the devices described herein may include any suitable polymeric material, including biocompatible materials such as polyurethane or silicone. Other suitable polymers include but are not limited to polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like.

Some embodiments may be described using the expression "coupled" and "connected" along with their derivatives. These terms are not intended as synonyms for each other. For example, some embodiments may be described using the terms "connected" and/or "coupled" to indicate that two or more elements are in direct physical or electrical contact with each other. The term "coupled," however, may also mean that two or more elements are not in direct contact with each other, but yet still co-operate or interact with each other.

Although non-limiting, as used herein with respect to the devices herein, the term "proximal end" may refer to a portion of the device, or a portion of a component of the device, closest to a handle or user interface of the device. The term "distal end" may refer to a portion of the device, or a portion of a component of the device, farthest from the handle or user interface of the device.

As used herein, the singular forms "a," "an," and "the" are intended to include the plural forms as well, unless the context clearly indicates otherwise. It will be further understood that the terms "comprises" and/or "comprising," or "includes" and/or "including" when used herein, specify the presence of stated features, regions, steps elements and/or components, but do not preclude the presence or addition of one or more other features, regions, integers, steps, operations, elements, components and/or groups thereof.

Furthermore, the terms "substantial" or "substantially," as well as the terms "approximate" or "approximately," can be used interchangeably in some embodiments, and can be described using any relative measures acceptable by one of skill. For example, these terms can serve as a comparison to a reference parameter, to indicate a deviation that will still provide the intended function. Although non-limiting, the deviation from the reference parameter can be, for example, in an amount of less than 1%, less than 3%, less than 5%, less than 10%, less than 15%, less than 20%, and so on.

Although specific embodiments have been illustrated and described herein, it should be appreciated that any arrangement calculated to achieve the same purpose may be substituted for the specific embodiments shown. This disclosure is intended to cover any and all adaptations or variations of various embodiments. It is to be understood that the above description has been made in an illustrative fashion, and not a restrictive one. Combinations of the above embodiments, and other embodiments not specifically described herein will be apparent to those of skill in the art upon reviewing the above description. Thus, the scope of various embodiments includes any other applications in which the above compositions, structures, and methods are used.

Still furthermore, although the illustrative method 500 is described above as a series of acts or events, the present disclosure is not limited by the illustrated ordering of such acts or events unless specifically stated. For example, some acts may occur in different orders and/or concurrently with other acts or events apart from those illustrated and/or described herein, in accordance with the disclosure. In addition, not all illustrated acts or events may be required to implement a methodology in accordance with the present disclosure.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed is:

1. A medical device, comprising:
   an endoscopic device operable to close an opening in a target tissue; and
   an actuator operable with the endoscopic device, the actuator including:
      a piston within a chamber, the piston comprising:
         a piston head engaged with an interior surface of the chamber; and
      a piston rod coupled to a tissue engagement component of the endoscopic device, wherein pressure from a fluid within the chamber actuates the tissue engagement component and
      a second piston within a second chamber, wherein the second chamber is fluidly connected with the chamber, wherein a first diameter (D1) of the first chamber is larger than a second diameter (D2) of the second chamber.

2. The medical device of claim 1, the actuator further comprising a valve connected to a fluid supply, wherein the valve controls a flow of the fluid through an inlet conduit and an outlet conduit, and wherein the inlet conduit and the outlet conduit are fluidly connected with the chamber.

3. The medical device of claim 1, wherein the tissue engagement component is a needle passer or an endoscopic stapler head.

4. The medical device of claim 3, the endoscopic stapler head comprising:
   a first jaw opposite a second jaw, wherein the piston rod is coupled to the first jaw; and
   a staple cartridge along the second jaw, wherein movement of the piston rod causes the first jaw to make or break contact with the staple cartridge.

5. The medical device of claim 1, the second piston comprising:
   a second piston head engaged with an interior surface of the second chamber; and
   a second piston rod extending from the second piston head, wherein the second piston head faces the piston head.

6. A system, comprising:
   an endoscope; and
   a device including an actuator operable to close an opening in a target tissue, the actuator including a piston within a chamber, the piston comprising:
      a piston head engaged with an interior surface of the chamber; and
   a piston rod coupled to a tissue engagement component of the endoscopic device, wherein pressure from a fluid within the chamber actuates the piston rod and the tissue engagement component; and
   a second piston within a second chamber, wherein the second chamber is fluidly connected with the chamber, wherein a first diameter (D1) of the chamber is larger than a second diameter (D2) of the second chamber.

7. The system of claim 6, the actuator further comprising a valve operable to control a flow of the fluid through an inlet conduit and an outlet conduit fluidly connected with the chamber.

8. The system of claim 6, the device comprising a suturing needle passer or an endoscopic stapler head.

9. The system of claim 6, wherein the device is a stapler head, the stapler head comprising:
   a first jaw opposite a second jaw, wherein the piston rod is coupled to the first jaw; and
   a staple cartridge along the second jaw, wherein movement of the piston rod causes the first jaw to make or break contact with the staple cartridge.

10. A method, comprising:
    inserting an endoscopic medical device within a patient, the endoscopic medical device comprising:
       an endoscopic device operable to engage a target tissue; and
       an actuator coupled to the endoscopic device, the actuator including:
          a piston within a chamber, the piston comprising:
             a piston head engaged with an interior surface of the chamber; and
             a piston rod coupled to a tissue engagement component of the endoscopic device; and
          a second piston within a second chamber, wherein the second chamber is fluidly connected with the chamber, wherein a first diameter (D1) of the chamber is larger than a second diameter (D2) of the second chamber;
    controlling an amount of a fluid within the chamber to actuate the piston rod and the tissue engagement component relative to the target tissue; and
    engaging the target tissue with the tissue engagement component to close an opening of the target tissue.

11. The method of claim 10, further comprising:
    engaging the target tissue using a stapler head, the stapler head including a first jaw opposite a second jaw, wherein the piston rod is coupled to the first jaw; and
    actuating the piston rod to close the first and second jaws about the target tissue to close the opening of the target tissue.

12. The method of claim 10,
    wherein a first diameter of the piston head is larger than a second diameter of a second piston head of the second piston; and
    actuating the second piston to increase a pressure of the fluid in the second chamber and the chamber.

* * * * *